(12) United States Patent  (10) Patent No.: US 6,746,134 B1
Guzorek                     (45) Date of Patent: Jun. 8, 2004

(54) UV ASSEMBLY WITH SWITCH

(75) Inventor: Steve Guzorek, Kinston, NC (US)

(73) Assignee: Field Controls, L.L.C., Kinston, NC (US)

( * ) Notice: Subject to any disclaimer, the term of this patent is extended or adjusted under 35 U.S.C. 154(b) by 96 days.

(21) Appl. No.: 09/898,858

(22) Filed: Jul. 3, 2001

(51) Int. Cl.⁷ ............................................. H01R 33/00
(52) U.S. Cl. ...................... 362/226; 362/96; 362/149; 362/382; 362/432
(58) Field of Search ......................... 362/96, 149, 432, 362/382, 226; 422/121, 24; 250/454.11, 435, 436; 96/224

(56) References Cited

U.S. PATENT DOCUMENTS

| 727,590 A | 5/1903 | Cole |
| 761,563 A | 5/1904 | Wagner |
| 2,786,936 A | 3/1957 | Appleton |
| 4,971,687 A | * 11/1990 | Anderson ..................... 210/85 |
| 5,030,124 A | 7/1991 | Lorentzon |
| 5,073,846 A | 12/1991 | Lin |
| 5,299,110 A | 3/1994 | Lin |
| 5,334,905 A | * 8/1994 | Ullrich .......................... 313/22 |
| 5,523,057 A | * 6/1996 | Mazzilli ...................... 422/121 |
| 5,866,076 A | * 2/1999 | Fencl et al. .................. 422/121 |
| 5,894,130 A | * 4/1999 | Bach ........................... 250/436 |
| 5,902,552 A | * 5/1999 | Brickley ...................... 422/121 |
| 6,372,186 B1 | * 4/2002 | Fencl et al. .................. 422/121 |

* cited by examiner

Primary Examiner—Sandra O'Shea
Assistant Examiner—Jacob Y. Choi
(74) Attorney, Agent, or Firm—McDermott, Will & Emery

(57) ABSTRACT

The present invention discloses an ultra-violet device for use with a heating, ventilation, and air conditioning system. The device includes an ultra-violet lamp mounted to a base having a switch for operating the lamp. The ultra-violet lamp and base couple to a mounting plate having a spring-loaded lever for engaging the switch of the base. The spring-loaded lever only engages the switch when the mounting plate, ultra-violet lamp, and base are properly configured. Thus, the ultra-violet device only operates when the device is properly configured.

1 Claim, 4 Drawing Sheets

UV ASSEMBLY WITH SWITCH

FIELD OF THE INVENTION

The present invention relates to an ultra-violet assembly for killing contaminants in an air duct. Specifically, the present invention relates to a mounting device for an ultra-violet lamp including a spring-loaded switch that prevents the lamp from being operated without first being properly mounted.

BACKGROUND OF THE INVENTION

It has long been known to use ultra-violet ("UV") light to control the growth of or kill contaminants known to exist within heating, ventilation, and air conditioning ("HVAC") systems. Accordingly, UV lamps have been installed in air ducts of HVAC systems for this purpose. Typically, UV lamps have been mounted within air ducts such that the UV light emitted by the lamp floods the interior of the air duct.

It is desirable to provide a feature to indicate to an installer of such devices that the assembly is properly installed, thus maximizing the amount of UV light emitted into the duct and minimizing, or eliminating, UV light emitted outside the duct. Accordingly, it would be desirable to provide an UV device for use in an HVAC air duct that must be properly mounted within the air duct to be operated.

SUMMARY OF THE INVENTION

It is one of the principal objectives of the present invention to provide an UV device capable of efficiently controlling or killing contaminants within an HVAC system.

It is another objective of the present invention to provide an UV device for use within an HVAC air duct that may be installed and/or operated by the typical homeowner.

It is yet another objective of the present invention to provide an UV device that may only be operated when properly installed for use within an HVAC air duct.

It is a further objective of the present invention to provide an UV device for maximizing UV light emitted into an HVAC duct.

It is still another objective of the present invention to provide an UV device for minimizing or eliminating UV light emitted outside of an HVAC duct.

These and other objectives of the present invention will become apparent upon examining the drawings and figures together with the accompanying written description thereof.

DETAILED DESCRIPTION OF THE DRAWINGS

Figure 1:
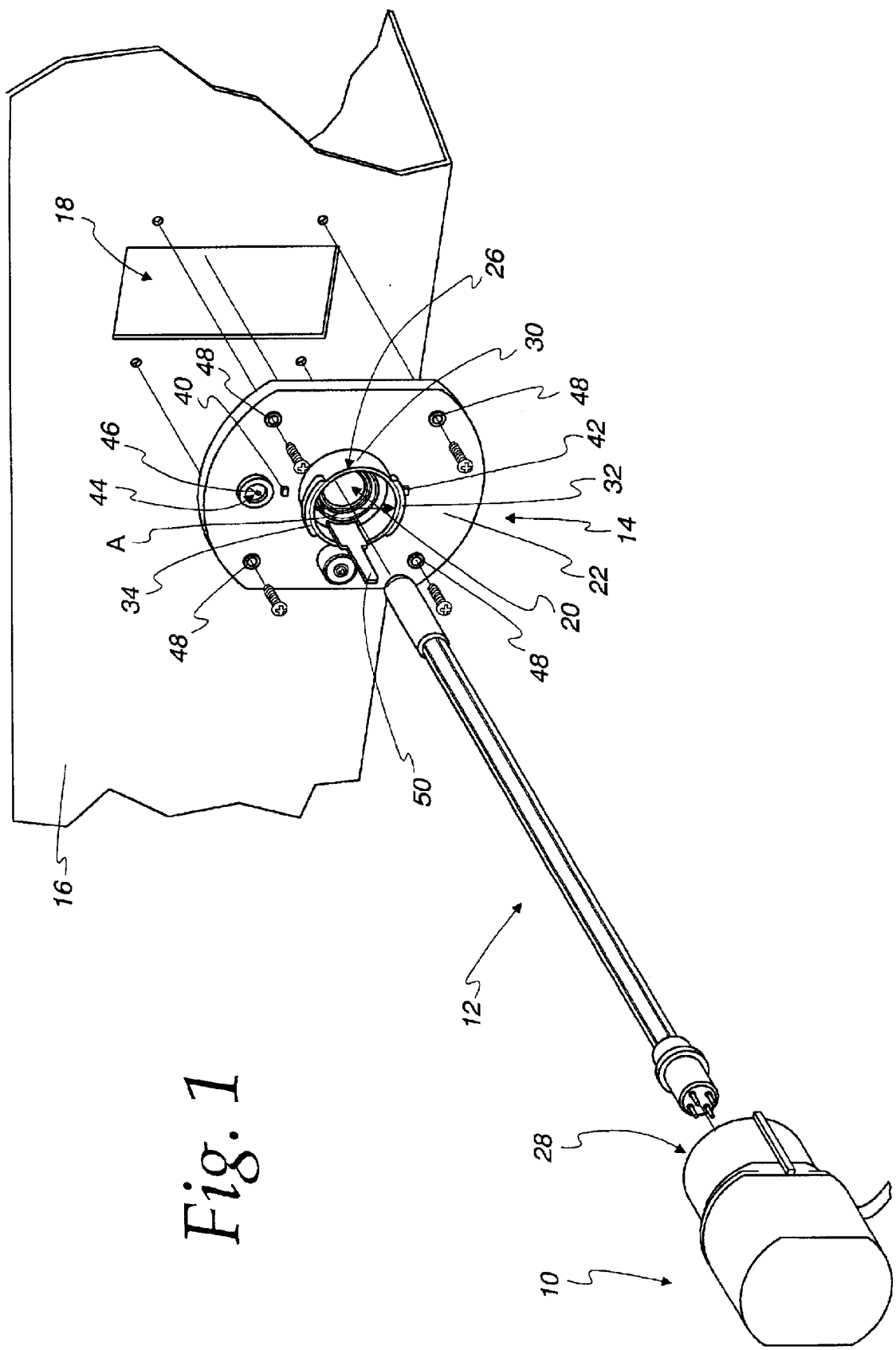
FIG. 1 is an exploded perspective view of the UV assembly including the power unit, an UV lamp, and the mounting bracket.

As shown in FIG. 1, the UV lamp assembly of the present invention includes a power unit 10 for powering an UV lamp 12 and a mounting bracket 14 for mounting to an air duct 16. Prior to mounting the mounting bracket 14 to the air duct 16, an opening 18 must be created in the air duct 16 for mounting the UV lamp 12 therethrough. The opening 18 can be created using a pair of tin snips, a jigsaw, or a similar cutting tool. Additionally, a template (not shown) can be employed in conjunction with the cutting tool to ensure the opening 18 is the proper size and shape for attaching the mounting bracket 14 and UV lamp 12. Alternatively, the opening 18 can be created in any manner apparent to one skilled in the art.

The mounting bracket 14 has an aperture 20 that, when properly installed, aligns with the opening 18 in the air duct 16. The UV lamp 12 extends through the aperture 20 into the interior of the air duct 16. The mounting bracket 14 has a front surface 22 and a back surface 24 (shown in FIG. 2). The mounting bracket 14 has a collar 26 on its front surface 22 for mating with a collar 28 the power unit 10.

As also shown in FIG. 1, the collar 26 of the mounting bracket 14 includes a cylinder 30 with two integrally formed raised lips 32, 34. The cylinder 30 is generally concentric with the aperture 20. The lips 32, 34 form an outer diameter A. The collar 26 and the lips 32, 34 of the mounting bracket 14 are used to couple the mounting bracket 14 and the power unit 10 together as described below.

The collar 26 of the mounting bracket 14 has a first stop 40 and a second stop 42 located approximately 180 degrees around the outer perimeter of the cylinder 30 from each other. In the embodiment shown in FIG. 1, the stops 40, 42 are integrally formed with the mounting bracket 14. However, the stops 40, 42 may be formed in any manner as would be apparent to one skilled in the art.

The mounting bracket 14 has a sight hole 44 with a lens 46 to enable an operator to look through the opening 18 and into the air duct 16 to determine whether the UV lamp 12 is operating properly. The lens 46 is preferably constructed of glass or plastic, however the lens 46 may be constructed of another material so long as the material permits an operator to view the interior of the air duct 16, while at the same time reduces the amount of UV light transmitting through the sight hole 44 to a level that is safe for operation by an operator.

The mounting bracket 14 shown in FIG. 1 has four mounting holes 48 for attaching the mounting bracket 14 to the air duct 16 using sheet metal screws or similar attaching means known in the art. Alternatively, the mounting bracket 14 may have any number of mounting holes 48 or may be attached to the air duct 16 in any other manner as would be apparent to one with skill in the art. The mounting bracket 14 attaches to the air duct 16 such that it completely covers the opening 18, preventing the transmission of UV light from inside the air duct 16 to the area surrounding the air duct 16. Additionally, sealing means, such as duct tape or other sealing means known in the art, may be used to seal the mounting bracket 14 to the air duct 16 to further prevent the transmission of UV light from inside the air duct 16 to the area surrounding the air duct 16.

The mounting bracket 14 has a lever 50 for engaging an electrical switch 52 (FIG. 4) in the power unit 10. The lever 50 is configured to engage the electrical switch 52 when the mounting bracket 14 is properly mounted to the air duct 16 and the power unit 10 is properly coupled to the mounting bracket 14 as described below.

Figure 2:
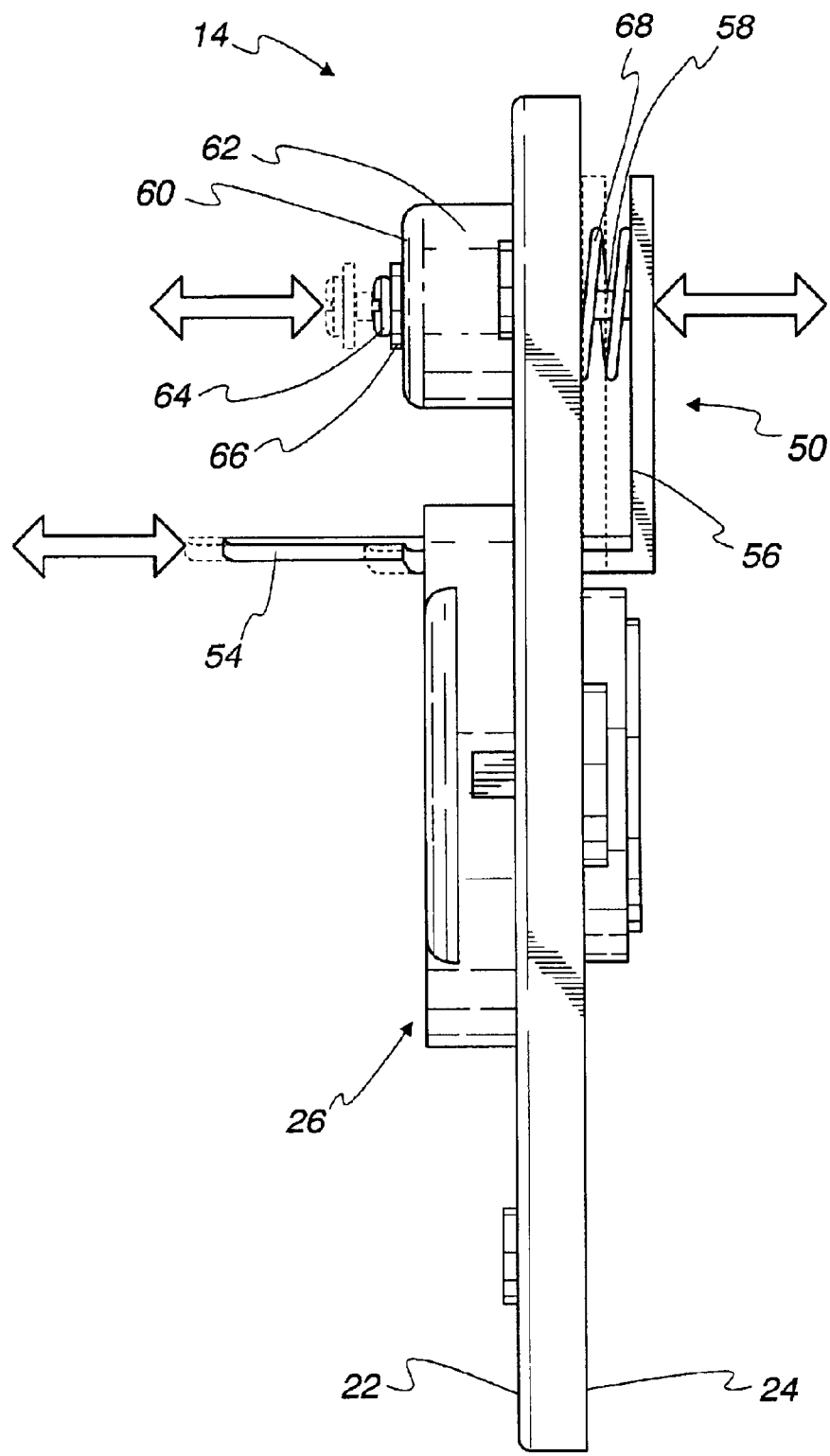
FIG. 2 is a top view of the mounting bracket of the UV assembly.

As shown in FIG. 2, the lever 50 has a switch-engaging portion 54, a biasing portion 56, and a coupling portion 58. The switch-engaging portion 54 extends through a slot (not shown) in the mounting bracket 14 and protrudes through the collar 26 of the mounting bracket 14. The coupling portion 58 of the lever 50 extends through a lever-coupling hole (not shown) in the mounting bracket 14.

The lever-coupling hole is located in an end cap 60 of a spring seating cylinder 62. A screw 64 attaches a washer 66 to the coupling portion 58 of the lever 50. The washer 66 has a larger diameter than the lever-coupling hole in order to secure the lever 50 to the mounting bracket 14. Alternatively, the lever 50 may be secured to the mounting bracket 14 in any other manner that allows the lever 50 to translate towards the front surface 22 of the mounting bracket 14, but does not allow the coupling portion 58 of the lever 50 to pass entirely through the lever coupling hole towards the back surface 24 of the mounting bracket 14.

A spring 68 is located along the coupling portion 58 of the lever 50 between the biasing portion 56 of the lever 50 and the end cap 60 of the spring seating cylinder 62. Generally, the spring 68 biases the biasing portion 56 of the lever 50 away from the back surface 24 of the mounting bracket 14. The washer 66 and the end cap 60 limit the distance the spring 68 may push the biasing portion 56 of the lever 50 away from the back surface 24 of the mounting bracket 14. However, when the mounting bracket 14 is properly affixed to the air duct 16, the spring 68 is compressed and the biasing portion 56 of the lever 50 contacts the back surface 24 of the mounting bracket 14. Consequently, when the mounting bracket 14 is properly mounted to the air duct 16 as described herein, the switch-engaging portion 54 of the lever 50 and the coupling portion 58 of the lever 50 extend further from the front surface 22 of the mounting bracket 14 than when the mounting bracket 14 is not properly mounted to the air duct 16. Alternatively, the lever 50 may be configured to bias towards the front surface 22 of the mounting bracket 14 when properly mounted to the air duct 16 in any manner apparent to one skilled in the art, including embodiments that do not include the spring 68.

As shown in FIG. 1, the opening 18 in the air duct 16 is dimensioned to provide an opening for use with the aperture 20 and the sight hole 44 of the mounting bracket 14, while not interfering with the portion of the air duct 16 necessary to contact the biasing portion 56 of the lever 50 and compress the spring 68 when the mounting bracket 14 is properly mounted to the air duct 16.

Figure 3:
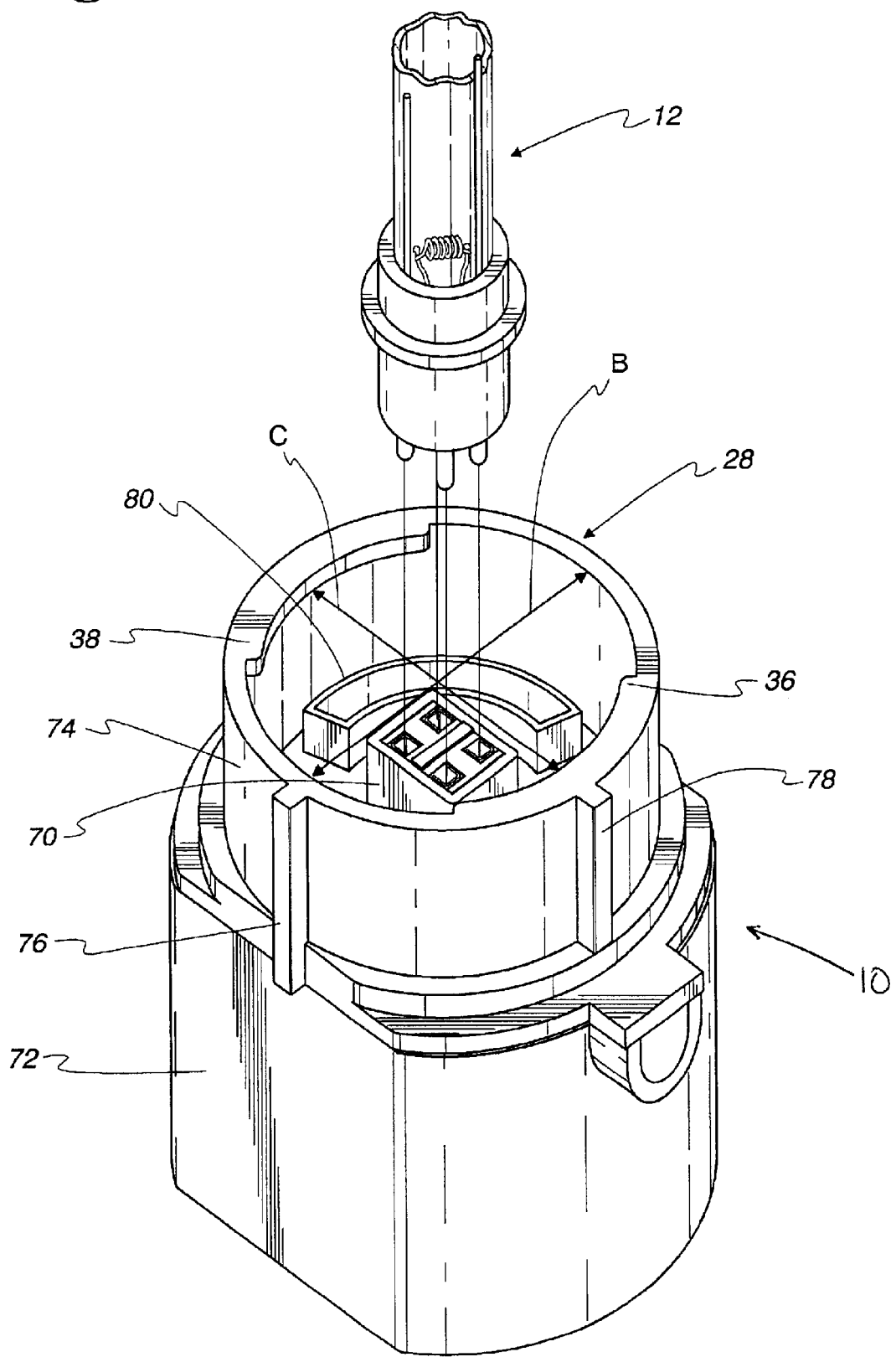
FIG. 3 is an exploded perspective view of the power unit and an UV lamp of the UV assembly.

As shown in FIG. 3, the UV lamp 12 couples to a lamp-mounting socket 70 in the power unit 10. A housing 72 encapsulates a ballast (not shown) for powering the UV lamp 12. The housing 72 in FIG. 3 is constructed from plastic, however the housing 72 may be constructed of another structural material. For example, as an alternative to plastic, the housing 72 may be constructed from metal. The UV lamp 12 can be a 120 Volt, 30 Watt, 0.5 Amp, 60 Hz, UV lamp such as the UV lamp sold under part number 46365402 by Field Controls (Kinston, N.C.) or another UV lamp 12. The ballast may be any ballast appropriately matched to power the UV lamp 12 used in the power unit 10. It is important that the ballast and the UV lamp 12 are appropriately matched because each UV lamp 12 requires a particular ballast for proper operation.

As described above with reference to FIG. 1, the power unit 10 has a collar 28 including a mounting cylinder 74. The two lips 36, 38 of the power unit 10 are integrally formed to the mounting cylinder 74. The collar 28 also includes a first ridge 76 and a second ridge 78 located along the length of the outer surface of the mounting cylinder 74. In the embodiment shown in FIG. 3, the two ridges 76, 78 are located approximately 90 degrees along the circumference of the mounting cylinder 74 from each other. The ridges 76, 78 are used to guide the coupling of, and limit the rotation of, the power unit 10 with respect to the mounting bracket 14 as described below. Other embodiments of the collar 28 are contemplated.

The mounting cylinder 74 of the power unit 10 has an inner diameter B. The lips 36, 38 of the power unit 10 form an inner diameter C. Diameter C is smaller than diameter B. Additionally, diameter A of the lips 32, 34 of the mounting bracket 14 is larger that diameter C, but smaller than diameter B. The relationship between these three diameters allows the collar 28 of the power unit 10 to couple to the collar 26 of the mounting bracket 14.

To couple the power unit 10 to the mounting bracket 14, the collar 28 of the power unit 10 may be positioned around the collar 26 of the mounting bracket 14. The cylinder 30 and the lips 32, 34 of the mounting bracket 14 are designed to permit the collar 28 and the lips 36, 38 of the power unit 10 to completely surround the collar 26 of the mounting bracket 14. Once positioned in this configuration, the power unit 10 may then be rotated with respect to the mounting bracket assembly such that the lips 36, 38 of the power unit 10 fit behind the lips 32, 34 of the mounting bracket 28. Consequently, when the lips 32, of the mounting bracket 14 are positioned behind the lips 36, 38 of the power unit 10, the power unit 10 and the mounting bracket 14 are securely coupled together. This position is hereinafter referred to as the "secured position".

The stops 40, 42 of the mounting bracket 14 are provided, along with the ridges 76, 78 of the power unit 10, to guide the coupling of, and limit the rotation of, the power unit 10 with respect to the mounting bracket 14. For example, in the embodiment shown in FIG. 1, the coupling portion 26 of the power unit 10 may be positioned to completely surround the collar 26 of the mounting bracket 14 with the first ridge 76 positioned just to the right hand side of the first stop 40, as seen from the perspective of an operator facing the front surface 22 of the mounting bracket 14. From this position, the power unit 10 may be rotated clockwise, again as seen from the perspective of an operator facing the front surface 22 of the mounting bracket 14, until the second ridge 78 contacts the second stop 42, placing the power unit 10 and mounting bracket 14 in the secured position.

Figure 4:
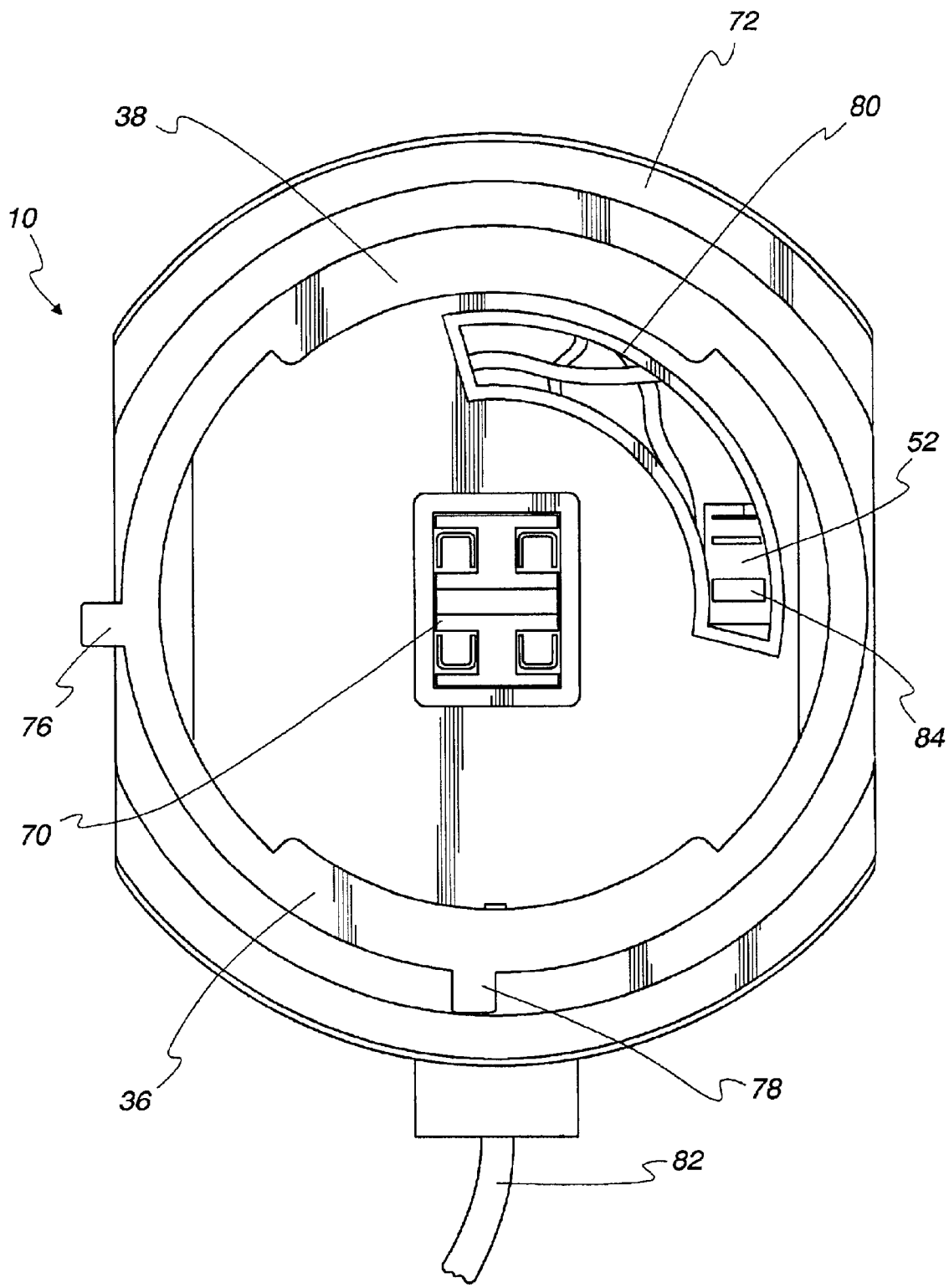
FIG. 4 is a front view of the power unit of the UV assembly.

As shown in FIG. 4, the electrical switch 52 is located in a switch channel 80 in the power unit 10. The electrical switch 52 couples an alternating current ("AC") cord 82 to the ballast and is used to control the supply of electricity to the ballast and ultimately to the UV lamp 12 mounted to the UV lamp mounting socket 70. The electrical switch 52 shown in FIG. 4 is a spring-loaded, snap action, single pull, single throw micro-switch, having an operating portion 84 for positioning the switch in either an "on position" or an "off position". The operating portion 84 is spring loaded to be biased towards the off position. The operating portion 84 can be depressed to position the electrical switch 52 in the on position. The switch channel 80 is adapted for use in conjunction with the switch-engaging portion 54 of the lever 50 as described below. The electrical switch 52 can be a snap-action, single pull, single throw, micro-switch such as the micro-switch sold by Zippy Technology Corp. (Shin-Tien City, Taipei Hsien, Taiwan, R.O.C.).

When the power unit 10 and the mounting bracket 14 are coupled together as described above with reference to FIG. 1, the lever 50 is positioned such that the switch-engaging portion 54 of the lever 50 is located within the switch channel 80 of the power unit 10. In the secured position, the switch-engaging portion 54 of the lever 50 is located in line with the operating portion 84 of the electrical switch 52. The switch-engaging portion 54 of the lever 50 is designed to engage the operating portion 84 of the electrical switch 52 when the power unit 10 and the mounting bracket 14 are coupled in the secured position and the biasing portion 56 of the lever 50 is held against the back surface 24 of the mounting bracket 14. When the biasing portion 56 of the lever 50 is in any position other than directly against the back surface 24 of the mounting bracket 14, the switch-engaging portion 54 of the lever 50 does not extend far enough from the front surface 22 of the mounting bracket 14 to engage the operating portion 84 of the electrical switch 52. Thus, if the power unit 10 and mounting bracket 14 are coupled in the secured position prior to properly mounting the mounting bracket 14 to the air duct 16, the lever 50 does not extend deep enough into the switch channel 22 in the power unit 10 to engage the electrical switch 52. However, when the mounting bracket 14 is properly attached to an air duct 16, and the power unit 10 is properly coupled to the mounting bracket 14 in the secured position, the biasing portion 56 of the lever 50 is pressed against the back surface 24 of the mounting bracket 14, the spring 68 is compressed, and the switch-engaging portion 54 of the lever 50 extends deep enough into the switch channel 22 to engage the operating portion 84 of the electrical switch 52. Thus, the UV lamp 12 will only operate when the power unit 10 is properly coupled to the mounting bracket 14 in the secured position and the mounting bracket 14 is properly affixed to the air duct 16.

It should be noted that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. An ultra-violet lamp device for mounting an ultra-violet lamp to an air duct, comprising:

a power unit having electrical circuitry for operating the ultra-violet lamp, said circuitry including an ultra-violet lamp socket and a switch; and a mounting bracket having a back surface for mounting to the air duct, a lever including a biasing portion and a switch-engaging portion and biasing means for biasing said lever away from said switch, wherein said biasing portion biases said lever towards a first position such that said biasing portion extends away from said back surface of said mounting bracket and said switch-engaging portion does not engage said switch, further wherein securing said mounting bracket to the air duct places said lever in a second position such that said switch-engaging portion engages said switch and said biasing portion does not extend away from said back surface of said mounting bracket.

\* \* \* \* \*